United States Patent [19]

Smith et al.

[11] Patent Number: 4,548,583

[45] Date of Patent: Oct. 22, 1985

[54] BONDING TO CALCIFIED TISSUES

[75] Inventors: Dennis C. Smith, Toronto; Rolf Maijer, Duncan, both of Canada

[73] Assignees: Dennis Smith Consulting Ltd., Toronto; Romada Holdings Ltd., Duncan, both of Canada

[21] Appl. No.: 545,881

[22] Filed: Oct. 27, 1983

Related U.S. Application Data

[63] Continuation-in-part of Ser. No. 424,051, Sep. 27, 1982, which is a continuation of Ser. No. 235,166, Sep. 27, 1981, Pat. No. 4,382,792.

[51] Int. Cl.[4] ............................................. A61K 6/08
[52] U.S. Cl. ................................... 433/228.1; 106/35
[58] Field of Search ..................... 106/35; 260/998.11; 523/118; 433/180, 183, 217, 228

[56] References Cited

U.S. PATENT DOCUMENTS

| | | | |
|---|---|---|---|
| 3,655,605 | 4/1972 | Smith | 106/35 |
| 3,751,391 | 8/1973 | Smith | 106/35 |

*Primary Examiner*—Lorenzo B. Hayes
*Attorney, Agent, or Firm*—Sim & McBurney

[57] ABSTRACT

Bonding to calcified tissues, including human teeth, tooth dentine and bone, is achieved through the medium of crystal growth adhered to the tissue. The crystals preferably comprise gypsum crystals which are formed by contacting the tissue surface with a mildly acidic solution containing sulphate ions. An uncured liquid resin is applied to the crystal growth and is cured to achieve adhesion by micromechanical interlock with the crystal growth and by superficial penetration of the tissue surface.

6 Claims, No Drawings

BONDING TO CALCIFIED TISSUES

REFERENCE TO RELATED APPLICATION

This application is a continuation-in-part of our copending application Ser. No. 424,051 filed Sept. 27, 1982, which itself is a continuation of copending Ser. No. 235,166 filed Sept. 27, 1981 (now U.S. Pat. No. 4,382,792).

FIELD OF INVENTION

The present invention relates to the bonding of materials to calcified surfaces.

BACKGROUND TO THE INVENTION

One of the major problems in surgical reconstruction of disease-damaged calcified tissues is the attachment of prosthetic or restorative materials to the tissue surface. This is a particular problem in the restoration of teeth since the functional mechanical, thermal and environmental stresses on the restoration interface usually lead to interfacial leakage between the restoration and the tooth when the restorative material is held in place merely by gross mechanical interlocking. This leakage may lead to penetration of bacteria and/or bacterial by-products along the tissue-material interface and a renewed process of dental decay. The concept of an adhesively-bonded prosthetic and restorative material has been extensively investigated in recent years but a reliable long term bond has been found to be difficult to establish under practical clinical conditions. Further, the use of chemically-active materials to develop chemical bonding at the adhesive interface may pose biocompatibility problems. The development of an attachment mechanism which would allow functional stress transfer across the interface between reconstructive materials and calcified tissues and also minimize leakage in situations such as tooth restoration, therefore, would be extremely beneficial in many medical and dental procedures.

In dentistry a widely used mechanism for attachment of polymerizable resin materials is the so-called acid etch technique. In this procedure, the tooth enamel surface is treated for about one minute with an acid solution or gel, usually 30 to 50% phosphoric acid. This treatment results in dissolution of the outer layer of the enamel to a depth of around 20 micrometers and the production of a clean etched porous surface. When a fluid polymerizable resin composition is placed on the etched surface, capillary action draws the monomers into the surface porosity to a depth of as much as 100 micrometers. After setting of the resin composition by chemical activation or radiation-induced polymerization, a strong bond of the resin to the tooth is induced by virtue of the extensive micromechanical interlocking created through penetration of the resin into the many pores in the etched surface of the enamel. Such a bond is as strong as the weaker of the resin and the enamel surface. This acid-etch technique has been used to attach resin coatings to teeth to seal the fissures in the biting surfaces to prevent decay and to provide facings which improve the aesthetic appearance of the teeth. Another preventive dentistry application of the acid-etch technique is to bond orthodontic attachments directly to the tooth in order to remove teeth within the jaws. For restorative purposes, acid-etching is used to improve the bond of restorative resins to fractured teeth and to minimize leakage around composite resin fillings. Still other applications include the splinting of loose teeth and temporary tooth replacement.

Although the acid-etch technique has proved to be extremely useful, certain disadvantages have become apparent. Among these are the loss of a significant depth of the outer enamel which contains most of the anticariogenic fluoride and the difficulty of removing bonded orthodontic attachments because of the deep penetration of resin into the etched enamel surface. In the latter application, the clinical removal of the attached resin consumes considerable time and can result in surface damage to the tooth surface because of the instrumentation needed to remove the assimilated resin.

SUMMARY OF INVENTION

In accordance with the present invention, there is provided a method of bonding materials to teeth and other calcified tissues which overcomes the disadvantages of the acid-etch technique and which has other advantages. The inventive procedure involves the formation on the tooth surface of an adherent crystalline deposit which has morphological characteristics permitting fluid materials, such as, polymerizable resins, to flow around the individual crystals, so that, after setting, the crystals act as anchoring points for the resin layer to the tooth surface. Formation of the crystal deposit involves interaction with the outer layer of the tooth surface, resulting, at the same time, in a clean wettable enamel surface which allows only superficial penetration by the bonding resin.

The bonding of the resin to the tooth, therefore, is achieved by micromechanical interlocking of the resin with the crystal growth in the tooth surface and superficial penetration of resin into the treated surface. By the proper choice of crystal growth characteristics, a bond strength of dental resins to tooth enamel surfaces can be achieved which is equivalent to the acid-etch technique, while at the same time minimizing enamel loss and permitting easy removal and clean-up when debonding is necessary, thereby overcoming the disadvantages of the acid-etch technique. Fluoride may be incorporated within the crystal deposit so as to provide resistance to decay and to demineralization at the tooth surface.

The crystal growth procedure of this invention is useful in all the clinical situations where the acid-etch technique is used. In addition, the present invention is applicable as a general bonding method to all types of calcified tissues, including tooth dentine and bone.

BRIEF DESCRIPTION OF DRAWINGS

FIGS. 1 to 4 are scanning electron micrographs of crystal growth formed on tooth enamel.

DESCRIPTION OF PREFERRED EMBODIMENTS

In a preferred embodiment of the invention, crystal growth on the calcified tissue surface is produced by interaction with a solution containing ionic species which result in an outgrowth of insoluble crystalline calcium salts which are bonded to the tissue surface. In order to confine the reaction to a specific area of tissue, the solution is often provided in a viscous or gel-like form to limit flow and surface reaction during application of the solution. After completion of crystal growth, which occurs rapidly, typically in about 30 seconds to about 6 minutes, the reactant solution is washed away and the tissue surface is dried prior to the application of resin or other bonding agent.

In order to facilitate the crystal growth, the solution usually is mildly acidic in order to effect a slight chemical reaction with the tissue surface to release calcium ions therefrom which then form a salt with the crystal-forming ionic species in the solution, the salt depositing in crystalline form. The crystals are nucleated within the tissue surface and thereby are firmly attached to it. The removal of calcium ions from the tissue surface to effect crystal formation involves considerably less damage to the surface when compared to the acid-etch technique.

The crystal growth generally is needle-like and occurs in random directions with respect to the tooth surface in dense formation, causing the intermeshing of crystals which enhances the anchoring capability of the crystal growth. Gypsum crystals usually are about 10 to about 25 micrometers long and about 2 to about 5 micrometers thick.

In forming the crystal growth, too great a density should generally not be permitted to form, otherwise this inhibits penetration of the orthodontic resin to the tooth surface, and inadequate bond strengths result as well as leakage at the resin-tooth interface. Excess growth can, however, be washed away by vigorous washing action and the residual nucleated surface used to achieve the desired micromechanical interlock with cured resin.

One convenient agent for effecting the crystal formation procedure used in this invention is an aqueous solution of polyacrylic acid containing sulphate ions. The polyacrylic acid may have a molecular weight of from 1,000 to 100,000 and a concentration of from about 10 to about 60%. In this instance, the crystal growth consists of gypsum crystals ($CaSO_4.2H_2O$). In order to achieve significant crystal growth, the solution contains at least about 1% of sulphate ions, with the upper limit of sulphate concentration being limited by solubility considerations and the desire to avoid over-etching of the tooth surface. The application of a drop of polyacrylic acid containing the sulphate ion to tooth enamel results in the formation of a dense growth of needle-shaped gypsum crystals having a spherulitic habit. The viscosity and reactivity of the solution may be varied by varying the concentration and/or molecular weight of the polyacrylic acid.

The polyacrylic acid may be used as the carrier medium for other ionic species, such as, phosphate, oxalate or tartrate, or in some cases may be omitted entirely. The ionic species may be used in the form of their free acid, for example, sulphuric acid or oxalic acid, or in the form of their salts, for example, ammonium salts.

Materials other than polyacrylic acid can be used as a carrier medium for the ionic species and for retaining the solution at a desired location on the tooth surface. For example, high viscosity methyl cellulose may be used.

EXAMPLES

EXAMPLE 1

Solutions of polyacrylic acid of molecular weights varying from 5,000 (5T) to 80,000 (80T) of solution concentrations of 20 to 50 percent were formed by aqueous polymerization of acrylic acid using ammonium persulphate as initiator. These solutions were applied to calcified tissue.

Scanning electron microscopy showed a copious growth of gypsum crystals with all solutions containing more than about 1 percent sulphate ions. Solutions containing less than this amount or dialysed free of sulphate ions (D) did not produce crystal growth. However, upon addition of the appropriate amount of sulphate ions, in the form of sulphuric acid or ammonium sulphate, crystal growth occurred.

In all cases, crystal growth was complete in a period of 2 to 6 minutes. Four of the SEM's at $2,000 \times$ magnification for 5T polyacrylic acid solutions are reproduced as FIGS. 1 to 4. The process conditions for each Figure is reproduced in the following Table I:

TABLE I

| FIG. | Solution Concentration (%) | Treatment Time (Mins) |
|---|---|---|
| 1 | 20 | 1 |
| 2 | 30 | 1 |
| 3 | 40 | 1 |
| 4 | 40 | 5 |

Calcium release from the tooth enamel surface was also determined and compared with that obtained with phosphoric acid solutions. The results are reproduced in the following Table II:

TABLE II

| Acid | Treatment Time (min) | Total $Ca^{++}$ Released (mean) (microg.) |
|---|---|---|
| 50T | 5 | 172 |
| 50T | 15 | 92 |
| 50T D | 5 | 122 |
| 50T D | 15 | 158 |
| 5T | 5 | 226 |
| 5T D | 5 | 148 |
| 50% $H_3PO_4$ | 5 | 1034 |
| 65% $H_3PO_4$ | 5 | 1518 |

It will be seen from the above Table II that the calcium released by acid-etch is many multiples of the calcium released by the polyacrylic acid solutions used in this invention. The calcium release values correspond approximately to an etch depth of about 7 micrometers for the polyacrylic acid and approximately 64 micrometers for the phosphoric acid.

EXAMPLE 2

Solutions of polyacrylic acid of molecular weight 12,000 (12T) containing at least 1% $SO_4^=$ were used to treat surfaces of extracted human premolar teeth for four minutes followed by washing and drying. Orthodontic brackets were bonded to the prepared tooth surfaces using two commercial orthodontic bonding resins. Similar specimens were prepared using the acid-etch technique using 37% orthophosphoric acid for 90 seconds. Details of the specimens are reproduced in the following Table III:

TABLE III

| Tooth Group | Tooth Conditioning | Bonding Agent |
|---|---|---|
| 1 | 20% 12T + 3.9% $SO_4$ | Adhesive A[1] |
| 2 | 20% 12T + 3.9% $SO_4$ | Adhesive B[2] |
| 3 | 40% 12T | Adhesive A |
| 4 | 40% 12T | Adhesive B |
| 5 | 37% phosphoric acid | Adhesive A |

TABLE III-continued

| Tooth Group | Tooth Conditioning | Bonding Agent |
|---|---|---|
| 6 | 37% phosphoric acid | Adhesive B |

Notes:
[1] Adhesive A is a commercial orthodontic bonding resin sold under the trademark "ORTHOMITE IIS" by Rocky Mountain Orthodontics, Colorado
[2] Adhesive B is a commercial orthodontic bonding resin sold under the trademark "AUTOTACH" by L. D. Caulk Co., Milford.

After the specimens were stored at 37° C. and 100% relative humidity for 24 hours, the tensile bond strengths were determined using an Instron testing machine.

The bond test results, in terms of the absolute force required to achieve fracture along the bracket-tooth interfacial bond and the force per unit area of bracket-tooth interfacial bond, are reproduced in the following Table IV:

TABLE IV

| Tooth Group | No. in Group | Fracture Force mean (kg) | S.D. | Range (kg) | Coeff. of Variation (%) | Bond Strength kg/cm$^2$ | PSI |
|---|---|---|---|---|---|---|---|
| 1 | 10 | 7.84 | 1.81 | 5.7 to 11.1 | 23.08 | 25.13 | 359.2 |
| 2 | 10 | 10.64 | 3.12 | 5.8 to 16.0 | 29.32 | 34.1 | 487.7 |
| 3 | 10 | 5.67 | 1.08 | 4.5 to 7.2 | 19.05 | 18.17 | 259.8 |
| 4 | 10 | 4.33 | 0.92 | 3.0 to 5.7 | 21.25 | 13.88 | 198.5 |
| 5 | 10 | 11.11 | 1.64 | 7.8 to 12.6 | 14.76 | 35.6 | 509.2 |
| 6 | 10 | 14.38 | 1.91 | 11.3 to 17.1 | 13.28 | 46.09 | 659.1 |

The results of Table IV show that the bond strength can be varied as desired depending on the conditions of formation of the crystal growth and can be made to approach that of the acid-etch technique.

EXAMPLE 3

A solution of polyacrylic acid of molecular weight 12,000 (12T) was prepared as described in Example 1 and adjusted to a concentration of 35%. The sulphate concentration was 3.7%. This solution was used to treat the labial surfaces of bovine teeth and orthodontic attachments were bonded as described in Example 2. The bonded assemblies were stored in water at 37° C. for varying periods of time up to 4 weeks before testing the tensile bond strength.

The results, in terms of the force per unit area of attachment-tooth interfacial bond required to achieve fracture, are reproduced in the following Table V:

TABLE V

| Treatment | Treatment Time (Water Storage) | Bonding Agent | Sample Size | Bond Strength mean (kg/cm$^2$) | S.D. | Coefficient of Variation (%) |
|---|---|---|---|---|---|---|
| None (Control) | 24 hrs | A[1] | 25 | 21.7 | 16.8 | 79.7 |
|  |  | B[2] | 28 | 18.7 | 16.6 | 88.8 |
| Acid Etch | 24 hrs | A | 16 | 107.1 | 26.6 | 24.8 |
|  |  | B | 25 | 117.0 | 26.0 | 22.2 |
| 12T | 24 hrs | A | 18 | 113.0 | 31.9 | 28.2 |
|  |  | B | 23 | 118.0 | 23.9 | 20.2 |
| 12T | 1 wk | A | 15 | 127.4 | 29.1 | 22.8 |
|  |  | B | 15 | 118.1 | 13.9 | 11.8 |
| 12T | 2 wk | A | 12 | 83.5 | 25.5 | 30.5 |
|  |  | B | 15 | 110.8 | 22.3 | 20.1 |
| 12T | 4 wk | A | 12 | 78.4 | 24.4 | 31.1 |
|  |  | B | 14 | 107.8 | 36.2 | 33.6 |
| Acid Etch | 1 wk | A | 14 | 117.1 | 34.1 | 29.1 |
|  |  | B | 15 | 130.3 | 20.6 | 15.8 |
| Acid Etch | 2 wk | A | 12 | 100.9 | 26.4 | 26.1 |
|  |  | B | 17 | 129.4 | 18.7 | 14.5 |
| Acid Etch | 4 wk | A | 12 | 87.7 | 38.1 | 43.4 |
|  |  | B | 15 | 112.2 | 18.3 | 16.3 |

Notes:
[1] Bonding Agent A is a commercial orthodontic bonding resin sold under the trademark "ORTHOMITE IIS" by Rocky Mountain Orthodontics, Colorado
[2] Bonding Agent B is a commercial orthodontic bonding resin sold under the trademark "CONCISE" by 3M Company, Minnesota The results of the above Table V illustrate that comparable results for the crystal bond technique are achieved when compared to the acid etch technique even after 4 weeks of water storage.

EXAMPLE 4

A bovine enamel surface was ground flat, washed and dried. The prepared surface was treated for 30 seconds with a 35 wt% solution of polyacrylic acid of molecular weight about 12,000 and containing 3 wt% of sulphate ion. The resulting crystal growth on the surface was washed and dried.

An orthodontic bonding resin, namely that sold under the trademark "SOLOTACH" by L. D. Caulk Co., Milford, Del., was mixed and manipulated according to the manufacturer's instructions and used to bond an orthodontic mesh based attachment to the prepared surface. After 24 hours storage in water at 37° C., the breaking load in tension of the bond of the attachment to the tooth was determined using an Instron Universal testing machine at a crosshead rate of 0.5 cm/min and the tensile bond strength calculated.

Five samples were tested and the mean bond strength result calculated to be 104 kg/cm$^2$, which is a very satisfactory result for the bonding of orthodontic attachments.

EXAMPLE 5

The procedure of Example 4 was repeated, except that a 2.6 wt% aqueous solution of sulphuric acid was used in place of the polyacrylic acid solution. Crystal growth again occurred and the tensile bond strength of an orthodontic resin to the surface was determined in Example 4. A mean bond strength of 102 kg/cm$^2$ was found.

The procedure of Example 4 again as repeated, in this case using a viscous methyl cellulose solution containing the 2.6 wt% sulphuric acid. A mean tensile bond strength of 92 kg/cm$^2$ resulted.

Example 6

The procedure of Example 4 was repeated, except that an aqueous methyl cellulose solution containing 1 wt% oxalic acid was used in place of the polyacrylic acid solution. Crystal growth believed to be calcium oxalate occurred. The mean tensile bond strength of an orthodontic resin to the surface, determined as described in Example 4, was 22 kg/cm$^2$. While this value is relatively low, it is satisfactory for application where temporary bonding only is required.

EXAMPLE 7

The procedure of Example 4 was repeated using a saturated aqueous solution of ammonium oxalate in place of the polyacrylic acid. The mean tensile bond strength for an orthodontic resin adhered to the resulting crystal growth was 44 kg/cm².

SUMMARY OF DISCLOSURE

In summary of this disclosure, the present invention provides a new method of bonding to teeth and other calcified tissues which is a substantial improvement over the conventional acid-etch technique. Modifications are possible within the scope of this invention.

What we claim is:

1. In a method of bonding materials to calcified tissues including human teeth, the improvement which comprises the sequential operation of initially forming a crystal growth of gypsum crystals having a length of about 10 to about 25 micrometers and a thickness of about 2 to about 5 micrometers adhered to and nucleated within a surface of said tissues, and subsequently interlocking said bonding with said crystal growth and said tissues.

2. A method of treating calcified tissues, which comprises:
contacting a surface of said tissue with a treatment agent for a time sufficient to form insoluble gypsum in crystalline form on the surface, and
subsequently removing spent treatment agent from the surface while leaving said crystalline salt adhered to the surface.

3. The method of claim 2 wherein said treatment agent comprises an aqueous solution of substantially non-flowing viscosity in which ionic species are dissolved capable of forming said crystalline salt, whereby said solution may be confined to a specific region of said surface, and said removal of said spent treatment agent is effected by washing spent solution from said surface after said crystalline salt is formed.

4. The method of claim 3 wherein said calcified tissue is human teeth.

5. The method of claim 4 wherein said solution additionally contains fluoride ions.

6. A method of treating calcified tissue, which comprises:
contacting a surface of said tissue with a treatment agent capable of forming gypsum crystals having a length of about 10 to about 25 micrometers and a thickness of about 2 to about 5 micrometers attached to and nucleated within the surface for a time sufficient to form said crystals, and
subsequently removing spent treatment agent from said surface to leave said crystals adhered to said surface.

* * * * *